United States Patent
Mori

(10) Patent No.: US 11,534,236 B2
(45) Date of Patent: Dec. 27, 2022

(54) ABLATION NEEDLE DEVICE AND HIGH-FREQUENCY ABLATION TREATMENT SYSTEM FOR TUMOR

(71) Applicant: Japan Lifeline Co., Ltd., Tokyo (JP)

(72) Inventor: Kenji Mori, Tokyo (JP)

(73) Assignee: Japan Lifeline Co., Ltd., Tokyo (JP)

(*) Notice: Subject to any disclaimer, the term of this patent is extended or adjusted under 35 U.S.C. 154(b) by 339 days.

(21) Appl. No.: 16/894,785

(22) Filed: Jun. 6, 2020

(65) Prior Publication Data
US 2020/0297408 A1 Sep. 24, 2020

Related U.S. Application Data

(63) Continuation of application No. PCT/JP2018/029352, filed on Aug. 6, 2018.

(30) Foreign Application Priority Data

Dec. 11, 2017 (JP) .............................. JP2017-236623

(51) Int. Cl.
*A61B 18/14* (2006.01)
*A61B 17/00* (2006.01)
*A61B 18/00* (2006.01)

(52) U.S. Cl.
CPC ............ *A61B 18/1477* (2013.01); *A61B 2017/00292* (2013.01); *A61B 2018/00023* (2013.01); *A61B 2018/00577* (2013.01); *A61B 2018/00821* (2013.01)

(58) Field of Classification Search
CPC .......... A61B 18/14; A61B 18/1477; A61B 2018/00023; A61B 2018/00577; A61B 2018/00821; A61B 2017/00292
See application file for complete search history.

(56) References Cited

U.S. PATENT DOCUMENTS

| | | | | |
|---|---|---|---|---|
| 5,951,546 A | * | 9/1999 | Lorentzen | A61B 18/1482 606/49 |
| 6,302,903 B1 | * | 10/2001 | Mulier | A61B 18/1477 606/41 |
| 7,077,842 B1 | * | 7/2006 | Cosman | A61B 18/148 606/41 |
| 11,272,978 B2 | * | 3/2022 | Mori | A61B 18/1477 |
| 2011/0054487 A1 | * | 3/2011 | Farnan | A61M 25/09 606/108 |

FOREIGN PATENT DOCUMENTS

JP 2017-127498 7/2017

* cited by examiner

*Primary Examiner* — Michael F Peffley
(74) *Attorney, Agent, or Firm* — Muramatsu & Associates

(57) ABSTRACT

An ablation needle device can maintain flexibility of an injection needle even when the length of an electrode constituted at a distal end portion thereof is increased and can perform cooling with small nonuniformity in the electrode during ablation. The ablation needle device includes: a hollow needle that is composed of a proximal end portion that is insulation-coated and a distal end portion constituting an electrode; a hub that includes a liquid injection port and a discharge port; an electric connector; a thermocouple; and cooling liquid introducing pipes each of which extends in the inside of the hollow needle, each of which has a distal end positioned in the inside of the distal end portion of the hollow needle, and each of which ejects liquid injected from the injection port from a distal end opening thereof.

12 Claims, 15 Drawing Sheets

VII—VII CROSS SECTIONAL VIEW

VI–VI CROSS SECTIONAL VIEW

IX—IX CROSS SECTIONAL VIEW

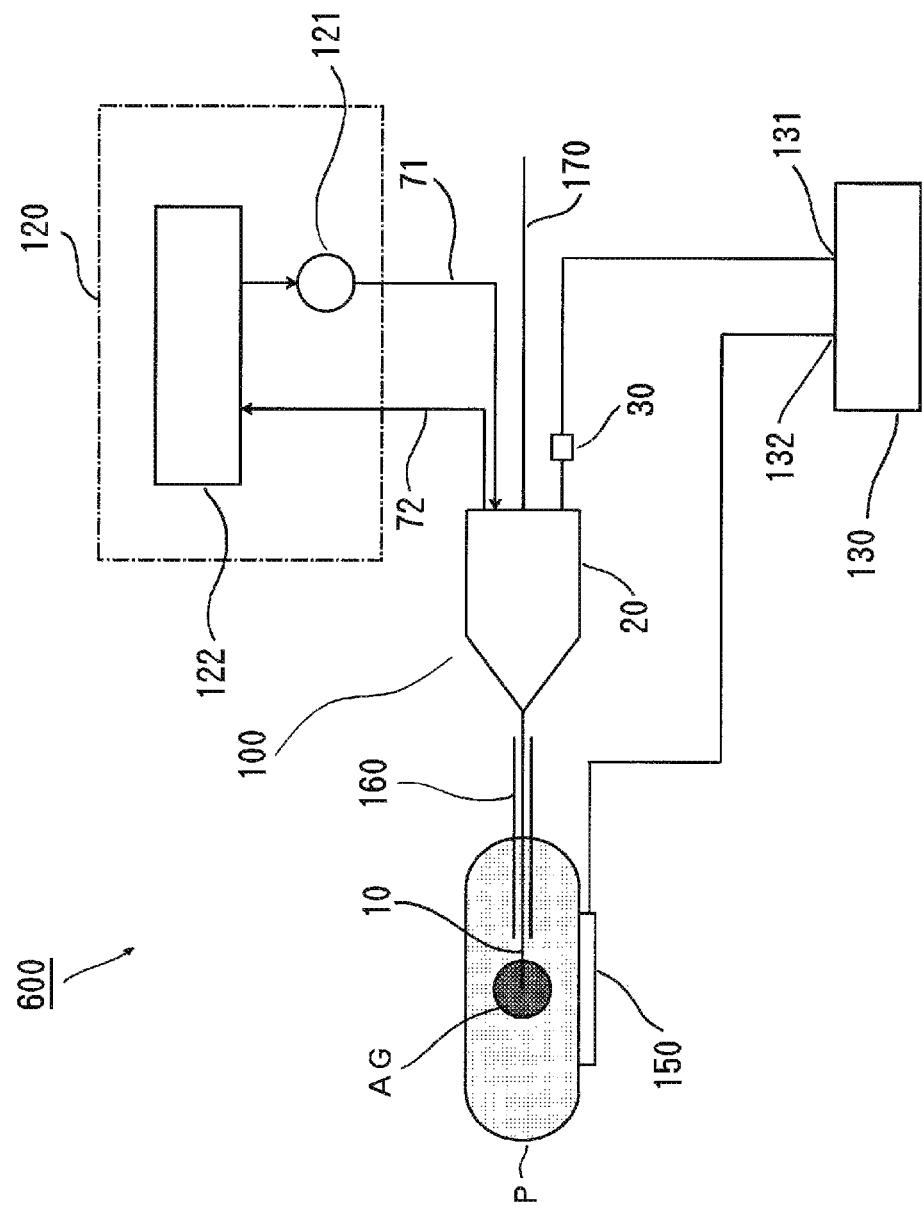

ABLATION NEEDLE DEVICE AND HIGH-FREQUENCY ABLATION TREATMENT SYSTEM FOR TUMOR

This is a continuation of International Application No. PCT/JP2018/029352 filed Aug. 6, 2018 which claims the benefit of priority based on Japanese Patent Application No. 2017-0236623, filed Dec. 11, 2017, the entire contents of which are incorporated herein by reference.

TECHNICAL FIELD

The present invention relates to an ablation needle device for performing an ablation treatment of a tumor such as an adrenal gland tumor and a high-frequency ablation treatment system for a tumor including the ablation needle device.

BACKGROUND ART

Primary aldosteronism is a hypertensive disease that occurs when an adenoma (tumor) that causes over-secretion of aldosterone, which is a vasopressor hormone, is formed in an adrenal gland.

As a treatment of primary aldosteronism, if over-secretion of aldosterone from one adrenal gland is detected, the adrenal gland having a tumor is removed.

If over-secretion of aldosterone from both adrenal glands is detected, because both adrenal glands cannot be removed, the patient needs to continue taking an antihypertensive agent.

Recently, as a treatment method for primary aldosteronism that causes over-secretion of aldosteronism, the following method has been introduced: after specifying an adrenal gland having abnormality by sampling blood from an adrenal gland vein (adrenal venous blood sampling) by using a catheter, the position of the adrenal gland is accurately identified from an X-ray image or the like, and a tumor is ablated by inserting a bipolar RF (radio frequency) needle from the back of the patient (see NPL 1 listed below).

However, although the treatment method described above is less invasive than an operation of removing an adrenal gland, the burden on a patient is still heavy.

Moreover, because the left adrenal gland is near the pancreas and the intestinal tract, a manipulation of inserting a bipolar RF needle into a tumor in the left adrenal gland from the back is anatomically difficult.

In order to solve such a problem, the inventor examined performing an ablation treatment by transvenously introducing an ablation needle into an adrenal gland, and proposed an ablation needle device that includes: an injection needle that is made of a metal and that is composed of a sharply-pointed tubular distal end portion and a tubular proximal end portion that has a lumen communicating with and having substantially the same diameter as a lumen of the distal end portion; and a grip portion that is attached to the proximal end side of the injection needle, in which the proximal end portion of the injection needle is given flexibility by forming a helical slit in at least a distal end region thereof, an outer surface of the proximal end portion is coated with a resin and the distal end of the distal end portion of the injection needle is closed, a plurality of fine holes that communicate with the lumen of the distal end portion are formed in an outer surface of the distal end portion including the closed part, and a liquid injection port for supplying liquid to the lumen of the injection needle is provided in the grip portion (see PTL 1 listed below).

In the ablation needle device, an electrode is constituted by the distal end portion of the injection needle that is not coated with a resin, and the length of the electrode constituted by the distal end portion is about 1 to 6 mm, which is preferable for treatment of a micro-adenoma.

With the ablation needle device, because the injection needle can be made flexible by reducing the rigidity in a distal end region of the proximal end portion of the injection needle to a certain level by forming the helical slit, the injection needle can be caused to follow the shape of a blood vessel extending to an adrenal gland without injuring a vascular wall and the distal end portion of the injection needle can be caused to reach a tumor site in the adrenal gland.

Moreover, because the plurality of fine holes that communicate with the lumen are formed in the outer surface of the distal end portion of the injection needle, a region around the distal end portion can be irrigated by ejecting the liquid, which is supplied to the lumen of the injection needle, from the plurality of fine holes, and a biological tissue or a thrombus can be prevented from adhering to a surface of the distal end portion (electrode) of the injection needle.

Accordingly, by using the ablation needle device, a transvenous ablation treatment, which is a new treatment method for primary aldosteronism, can be reliably performed.

CITATION LIST

Patent Literature (PTL) and Non-Patent Literature (NPL)

NPL 1: The Chemical Daily, Sep. 25, 2013
PTL 1: Japanese Unexamined Patent Application Publication No. 2017-127498

SUMMARY OF INVENTION

Technical Problem

For example, in a case where it is necessary to ablate the entirety of an adrenal gland, such as a case where the entirety of the adrenal gland has a tumor, it is desirable to increase the size of an ablation region to be ablated by using a high-frequency electric current. In order to increase the size of the ablation region, it is necessary to increase the length of the electrode (to, for example, about 20 mm).

However, because a slit is not formed in the electrode (the distal end portion of the injection needle) of the ablation needle device described in PTL 1, when the length of the electrode is increased, the rigidity of the injection needle including such an electrode increases and the flexibility decreases, the injection needle cannot follow the complex shape of a blood vessel, and therefore the injection needle may penetrate into a guiding catheter or a vascular wall while being introduced into an adrenal gland.

Therefore, it is desirable to provide an ablation needle device including a flexible and long electrode.

Moreover, as the length of the electrode of the ablation needle device is increased, it is necessary to increase the amount of cooling water (saline solution) that is irrigated in order to cool the electrode.

However, when a relatively large amount of cooling water for the size of an organ (adrenal gland) to be treated is irrigated, there is a risk of swelling or expansion of the organ, spreading of tumor tissues, and the like.

Furthermore, as the length of the electrode of the ablation needle device is increased, nonuniform cooling in the longitudinal direction of the electrode may occur.

The present invention has been made under the circumstances described above.

An object of the present invention is to provide an ablation needle device that can maintain the flexibility (bendability) of an injection needle including an electrode even when the length of the electrode constituted by a distal end portion of the injection needle is set to be large, that can sufficiently cool the electrode while avoiding a risk that occurs when cooling liquid is irrigated during ablation, and that can perform cooling with small nonuniformity in the longitudinal direction of the electrode.

Another object of the present invention is to provide an ablation needle device that can be particularly preferably used for a treatment method of performing a high-frequency ablation of an adrenal gland tumor by transvenously introducing an injection needle into an adrenal gland, and in particular, for a treatment method of ablating the entirety of an adrenal gland.

A still another object of the present invention is to provide a high-frequency ablation treatment system that can be preferably used for a treatment method of performing a high-frequency ablation of a tumor.

Solution to Problem (1) An ablation needle device according to the present invention is a needle device for performing a high-frequency ablation treatment of a tumor, comprising:
  a hollow needle that is made of a metal and that is composed of a proximal end portion having an outer surface that is insulation-coated with a resin and a distal end portion having an outer surface that is exposed and thus constituting an electrode;
  a hub that is attached to a proximal end side of the hollow needle and that includes a liquid injection port for injecting liquid for cooling the electrode (the distal end portion of the hollow needle) and supplying the liquid to an inside of the hollow needle, and a liquid discharge port for discharging liquid that has cooled the electrode and returned from the inside of the hollow needle;
  an electric connector that is electrically connected to the hollow needle in order to supply a high-frequency electric current to the electrode;
  a thermocouple that extends in the inside of the hollow needle in order to measure a temperature of a tissue around the electrode; and
  a plurality of cooling liquid introducing pipes each of which extends in an inside of the hub and the inside of the hollow needle, each of which has a distal end positioned in an inside of the distal end portion of the hollow needle, and each of which ejects liquid injected from the injection port from a distal end opening thereof,
  wherein the hollow needle is given flexibility by forming a helical slit in at least a distal end region of the proximal end portion of the hollow needle and the distal end portion adjacent thereto,
  wherein a liquid-tightness of the inside of the hollow needle is ensured by applying waterproofing to an inner surface of the hollow needle in at least a region in which the slit is formed in the distal end portion and by closing a distal end of the hollow needle, and
  wherein distal end opening positions of the plurality of cooling liquid introducing pipes differ from each other in a distal-proximal direction of the hollow needle.

With the ablation needle device having such a configuration, because the helical slit is formed not only in the proximal end portion of the hollow needle but also in the distal end portion constituting the electrode, the hollow needle (injection needle) including the electrode can be made flexible even when the length of the electrode is set to be large for the purpose of increasing the size of an ablation region, the hollow needle can be caused to follow the complex shape of a blood vessel without injuring a vascular wall and the like, and the electrode can be caused to reliably reach a target site.

Moreover, by ejecting cooling liquid from the distal end openings of the plurality of cooling liquid introducing pipes in the inside of the distal end portion of the hollow needle whose liquid-tightness is ensured, the electrode can be sufficiently cooled (inner cooling) while completely avoiding a risk that occurs when cooling liquid is irrigated.

Furthermore, because the distal end opening positions (ejection positions of cooling liquid) of the plurality of cooling liquid introducing pipes differ from each other in the distal-proximal direction of the hollow needle in the inside of the distal end portion of the hollow needle constituting the electrode, cooling with small nonuniformity in the longitudinal direction of the electrode can be performed even when the length of the electrode is set to be large.

(2) In the ablation needle device according to the present invention, preferably, the hub includes a liquid flow port that includes both of the injection port and the discharge port.

(3) The ablation needle device according to the present invention preferably comprises: a first cooling liquid introducing pipe that extends in the inside of the hub and the inside of the hollow needle, that has a distal end positioned in the inside of the distal end portion of the hollow needle, and that ejects liquid injected from the injection port from a distal end opening thereof; and
  a second cooling liquid introducing pipe that extends in the inside of the hub and the inside of the hollow needle together with the first cooling liquid introducing pipe, that has a distal end positioned in the inside of the distal end portion of the hollow needle, and that ejects liquid injected from the injection port from a distal end opening thereof,
  wherein a distal end opening position of the first cooling liquid introducing pipe and a distal end opening position of the second cooling liquid introducing pipe differ from each other in the distal-proximal direction of the hollow needle.

With the ablation needle device having such a configuration, because the distal end opening position (ejection position of cooling liquid) of the first cooling liquid introducing pipe and the distal end opening position (ejection position of cooling liquid) of the second cooling liquid introducing pipe differ from each other in the distal-proximal direction of the hollow needle in the inside of the distal end portion of the hollow needle constituting the electrode, cooling with small nonuniformity in the longitudinal direction of the electrode can be performed even when the length of the electrode is set to be large.

(4) In the ablation needle device described in (3), preferably, the distal end opening of the first cooling liquid introducing pipe is positioned in an inside of a vicinity of a distal end of the distal end portion of the hollow needle, and the distal end opening of the second cooling liquid introducing pipe is positioned in an inside of an approximately middle part (substantially middle part) or a vicinity of a proximal end of the distal end portion of the hollow needle.

With the ablation needle device having such a configuration, cooling liquid ejected from the distal end opening of the first cooling liquid introducing pipe can cool mainly a distal end part of the distal end portion (electrode) of the hollow needle, and cooling liquid ejected from the distal end opening of the second cooling liquid introducing pipe can cool mainly a proximal end part of the distal end portion (electrode) of the hollow needle.

(5) In the ablation needle device according to the present invention, preferably, the distal end of the hollow needle is closed by a distal end tip that is made of a resin, and a temperature measuring junction of the thermocouple is embedded in the distal end tip.

With the ablation needle device having such a configuration, because the temperature measuring junction of the thermocouple is embedded in the distal end tip made of a resin having low thermal conductivity, the temperature measuring junction is not easily influenced by temperature variation of the electrode (the distal end portion of the hollow needle), and can accurately measure the temperature of a tissue around the electrode.

(6) In the ablation needle device according to the present invention, preferably, a lumen tube that forms a guidewire lumen extends in the inside of the hollow needle.

With the ablation needle device having such a configuration, the electrode (the distal end portion of the hollow needle) can be caused to rapidly and reliably reach a target site by using a guidewire.

(7) In the ablation needle device according to the present invention, preferably, a length of the electrode constituted by the distal end portion of the hollow needle is 6 to 30 mm, and particularly 8 to 30 mm.

It is particularly effective to use the configuration of the present invention in an ablation needle device including such a long electrode.

(8) In the ablation needle device according to the present invention, preferably, a pitch of the slit formed in the hollow needle continuously or intermittently decreases in a distal end direction.

With such an ablation needle device, the rigidity of the hollow needle can be continuously or intermittently reduced in the distal end direction, and thus the needle device has particularly good operability during introduction of the hollow needle into a target site.

(9) In the ablation needle device according to the present invention, preferably, in at least the region in which the slit is formed in the distal end portion, the waterproofing is applied by forming a waterproof seal coating on the inner surface of the hollow needle.

With such an ablation needle device, because waterproofing can be reliably applied to the inner peripheral surface of a region of the distal end portion having the outer surface that is exposed (that is not resin-coated) and in which the slit is formed, the liquid-tightness of the inside of the hollow needle can be ensured.

(10) In the ablation needle device described in (9), preferably, the waterproof seal coating is formed by increasing a diameter of a heat-expandable resin tube, which is in a state of having been inserted to the inside of the hollow needle, by heating the heat-expandable resin tube.

(11) The ablation needle device according to the present invention can be preferably used for performing an ablation treatment of an adrenal gland tumor by transvenously introducing the hollow needle into an adrenal gland.

(12) A high-frequency ablation treatment system according to the present invention comprises: the ablation needle device according to the present invention;

a high-frequency electric power source device connected to the electric connector;

a patient plate connected to the high-frequency electric power source device;

a guiding catheter for guiding the distal end portion of the hollow needle to a vicinity of a target site; and a cooling liquid circulation mechanism that includes a cooling liquid supply pump that injects cooling liquid into the injection port of the hub in order to cool the electrode of the ablation needle device, and a recovery tank that recovers liquid that has cooled the electrode and returned from the inside of the hollow needle to the inside of the hub from the discharge port and cools the liquid again.

Advantageous Effects of Invention

With the ablation needle device according to the present invention, the hollow needle including the electrode can be made flexible even when the length of the electrode constituted by the distal end portion of the hollow needle is set to be large.

Moreover, during ablation, the electrode can be sufficiently cooled while completely avoiding the aforementioned risk, which occurs when cooling liquid is irrigated, by ensuring the liquid-tightness of the inside of the hollow needle and performing inner cooling.

Furthermore, efficient cooling with small nonuniformity in the longitudinal direction of the electrode can be performed even when the length of the electrode is set to be large.

With the high-frequency ablation treatment system according to the present invention, a high-frequency ablation treatment of a tumor can be reliably performed.

BRIEF DESCRIPTION OF DRAWINGS

FIG. 12 schematically illustrates the configuration of a high-frequency ablation treatment system according to the present invention.

DESCRIPTION OF EMBODIMENTS

<Ablation Needle Device>

Figure 1:
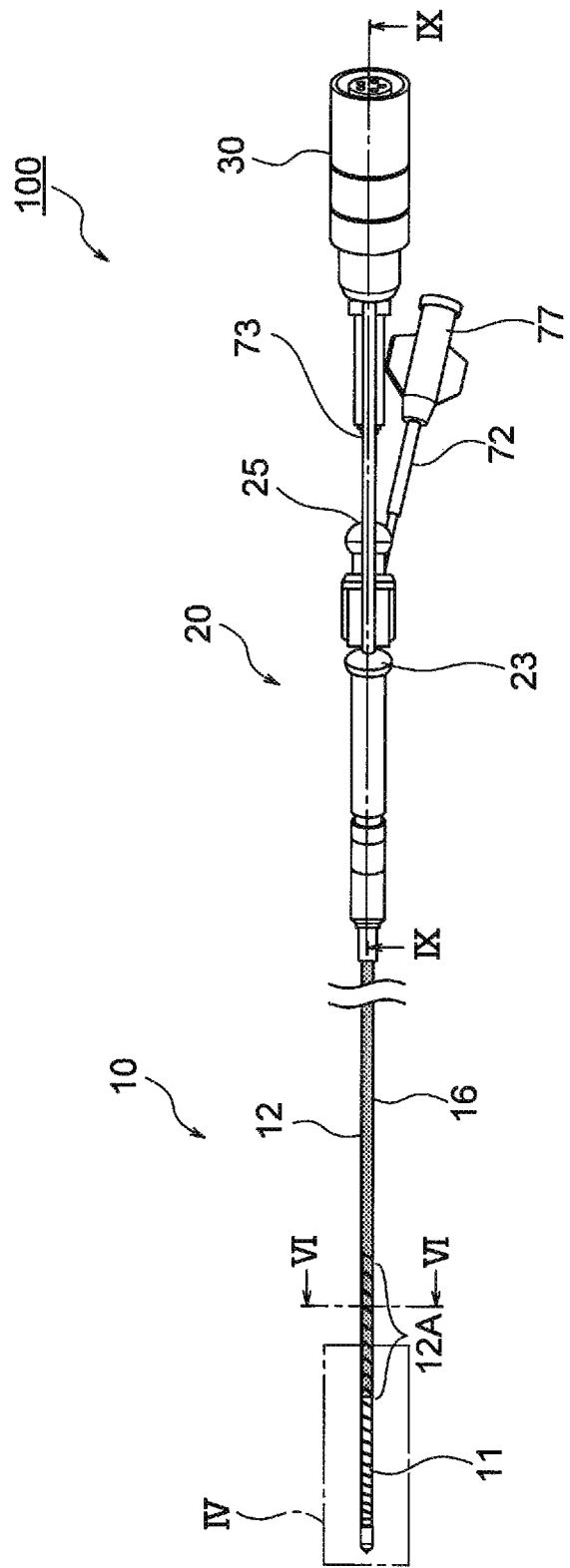
FIG. 1 is a front view illustrating an ablation needle device according to an embodiment of the present invention.

An ablation needle device 100 according to the present embodiment is an ablation needle device for performing a high-frequency ablation treatment of an adrenal gland tumor by transvenously introducing an injection needle (hollow needle) into an adrenal gland, including: a hollow needle 10 that is made of a metal and that is composed of a proximal end portion 12 having an outer surface that is insulation-coated with a resin 16 and a distal end portion 11 having an outer surface that is exposed and thus constituting an electrode; a hub (branched hub) 20 that is attached to a proximal end side of the hollow needle 10 and that includes a liquid flow port 21 (one port that includes both of a liquid injection port and a liquid discharge port), a connection port 23 of an electric connector, and a guidewire port 25; an electric connector 30 that is electrically connected to the hollow needle 10 in order to supply a high-frequency electric current to the electrode; a thermocouple 40 that is inserted to the inside of the hub 20 from the connection port 23 of electric connector in order to measure the temperature of a tissue around the electrode and that extends in the inside of the hub 20 and the inside of the hollow needle 10; a first cooling liquid introducing pipe 51 that extends in the inside of the hub 20 and the inside of the hollow needle 10, that has a distal end 511 positioned in the inside of the distal end portion 11 of the hollow needle 10, and that ejects cooling liquid injected from the flow port 21 to the inside of the hub 20 from a distal end opening thereof; a second cooling liquid introducing pipe 52 that extends in the inside of the hub 20 and the inside of the hollow needle 10 together with the first cooling liquid introducing pipe 51, that has a distal end 521 positioned in the inside of the distal end portion 11 of the hollow needle 10, and that ejects cooling liquid injected from the flow port 21 to the inside of the hub 20 from a distal end opening thereof; and a lumen tube 60 that extends in the inside of the hollow needle 10 and forms a guidewire lumen, wherein the hollow needle 10 is given flexibility by forming a helical slit 14 in a distal end region 12A of the proximal end portion 12 of the hollow needle 10 and the distal end portion 11 adjacent thereto, wherein the liquid-tightness of the inside of the hollow needle 10 is ensured by forming a waterproof seal coating 18 on an inner surface of the hollow needle 10 and by closing the distal end of the hollow needle 10 with a distal end tip 15 made of a resin, wherein a temperature measuring junction (temperature sensor) 45 of the thermocouple 40 is embedded in the distal end tip 15 and a distal end part of the lumen tube 60 extends through the distal end tip 15 and forms an opening, and wherein the distal end opening position of the first cooling liquid introducing pipe 51 and the distal end opening position of the second cooling liquid introducing pipe 52 differ from each other in the distal-proximal direction of the hollow needle 10.

In FIGS. 1 to 3 and FIGS. 9 to 11, 71 to 74 respectively denote extension tubes that extend out from the ports 21, 23, and 25 of the hub 20; and 76, 77, and 79 respectively denote connectors that are attached to proximal ends of the extension tubes 71, 72, and 74.

The ablation needle device 100 according to the present embodiment includes the hollow needle (injection needle) 10, the hub 20, the electric connector 30, the thermocouple 40, the first cooling liquid introducing pipe 51, the second cooling liquid introducing pipe 52, and the lumen tube 60.

The hollow needle 10 of the ablation needle device 100 is a hollow needle that is made of a metal and that is composed of the proximal end portion 12 having an outer surface that is insulation-coated with the coating resin 16 and the distal end portion 11 having an outer surface that is exposed and thus constituting an electrode.

Examples of a metal material of the hollow needle 10 include stainless steel, NiTi, β titanium, platinum iridium, and the like.

The outside diameter of the hollow needle 10 (the distal end portion 11 and the proximal end portion 12) is, for example, 0.55 to 3.0 mm, and preferably 0.7 to 2.0 mm.

The inside diameter of the hollow needle 10 (the distal end portion 11 and the proximal end portion 12) is, for example, 0.25 to 2.8 mm, and preferably 0.6 to 1.9 mm.

The length of the hollow needle 10 is, for example, 200 to 2200 mm, and preferably 600 to 1000 mm.

The outer surface of the proximal end portion 12 of the hollow needle 10 is insulation-coated with the coating resin 16, and thus a high-frequency electric current does not flow between the proximal end portion 12 and a patient plate.

The film thickness of the coating resin 16 is, for example, 10 to 100 μm, and preferably 20 to 40 μm.

The coating resin 16 is formed by decreasing the diameter of a heat-shrinkable resin tube, which is in a state that the proximal end portion 12 has been inserted to the inside thereof, by heating the heat-shrinkable resin tube.

Examples of a heat-shrinkable resin tube for forming the coating resin 16 include a polyether block amide copolymer resin (PEBAX (registered trademark)).

The outer surface of the distal end portion 11 of the hollow needle 10 is not resin-coated and is exposed.

Thus, a high-frequency electric current flows between the distal end portion 11 and the patient plate, and the distal end portion 11 functions as an electrode.

Figure 4:
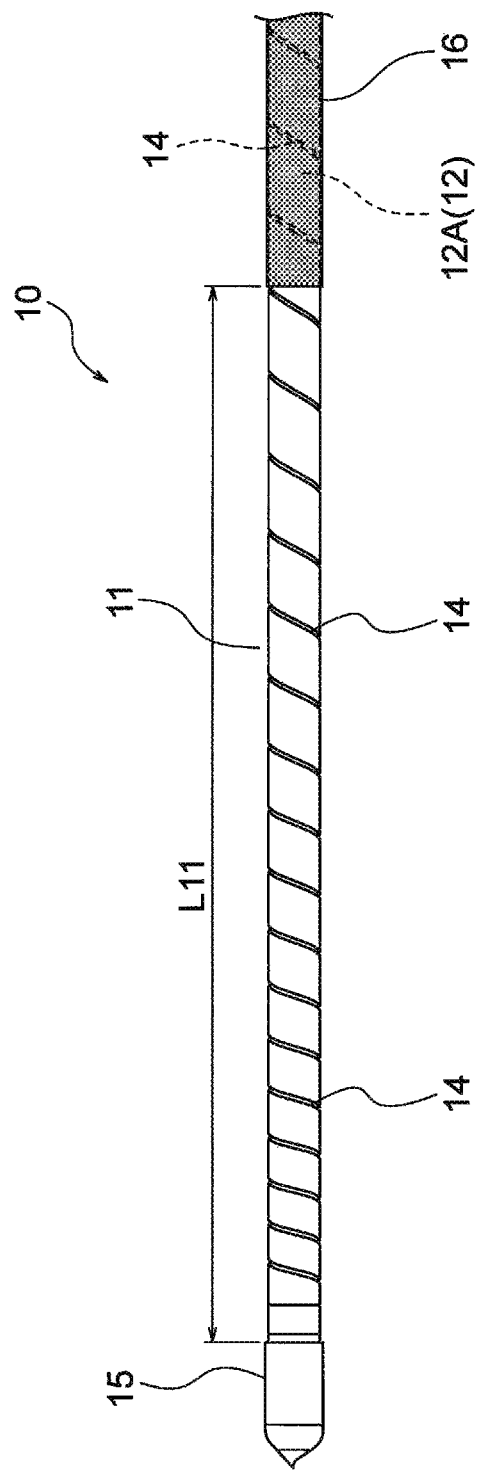
FIG. 4 is an enlarged partial front view of the ablation needle device illustrated in FIG. 1 (enlarged view of portion IV of FIG. 1).
Figure 5:
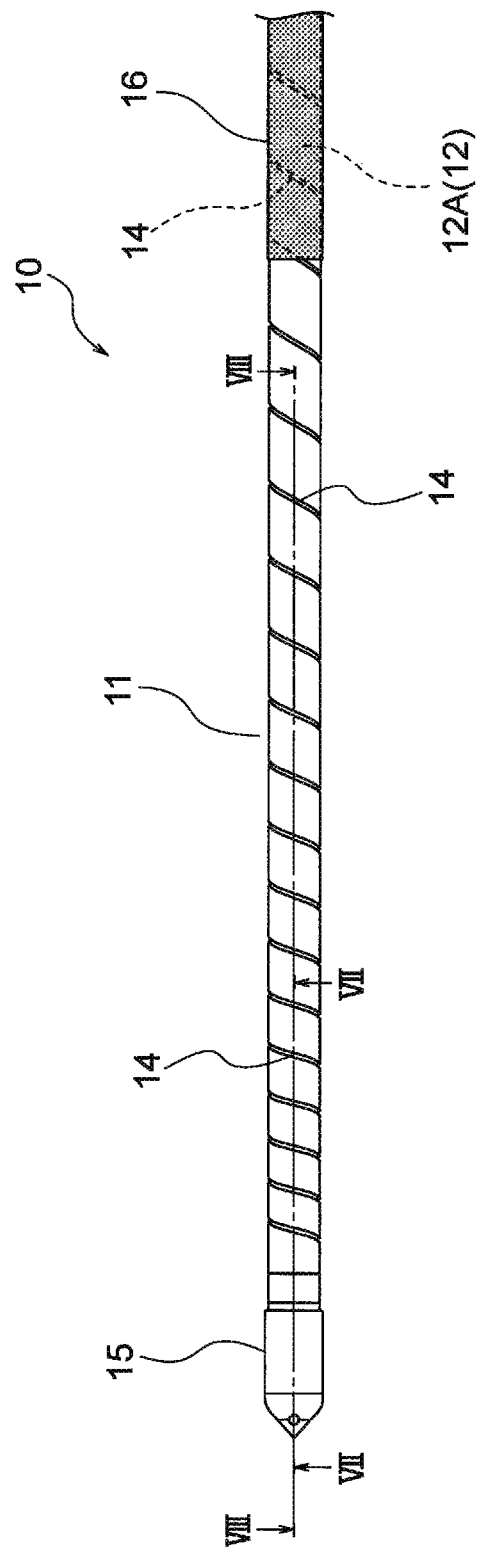
FIG. 5 is an enlarged partial front view of the ablation needle device illustrated in FIG. 1 (enlarged view of portion V of FIG. 2).

The length of the distal end portion 11 of the hollow needle 10 (L11 shown in FIG. 4) is preferably 6 mm or larger, more preferably 6 to 30 mm, and further preferably 8 to 30 mm; and a preferable example may be 20 mm.

When the length of the distal end portion 11 is 6 mm or larger, a heat generating region due to a high-frequency electric current (the size of an ablation region) can be increased, and a sufficient treatment effect can be obtained even when a treatment method of ablating the entirety of an adrenal gland is performed.

In the hollow needle 10, the helical slit 14 is formed in the distal end region 12A of the proximal end portion 12 and in the distal end portion 11 adjacent thereto.

Because the helical slit 14 is formed not only in the distal end region 12A of the proximal end portion 12 of the hollow needle 10 but also in the distal end portion 11 constituting an electrode, even when the length of the electrode (the distal end portion 11) is increased, the hollow needle 10 including the electrode has high flexibility (bendability) and can be easily caused to follow the shape of a blood vessel extending to an adrenal gland.

The length of the distal end region 12A, which is a region of the proximal end portion 12 in which the slit 14 is formed, is, for example, 50 to 800 mm, and preferably 100 to 600 mm.

The slit 14 in the distal end portion 11 need not be formed over the entire length of the distal end portion 11, as long as flexibility (bendability) of the hollow needle 10 including the electrode can be ensured. In the present embodiment, the slit 14 is not formed in a region within at least about 3 to 8 mm from the distal end, including a part to which the distal end tip 15 is attached.

A method for forming the slit 14 is not particularly limited, and laser machining, electrical discharge machining, chemical etching, cutting, or the like may be used.

The width of the slit 14 is, for example, 0.01 to 0.1 mm, and preferably 0.02 to 0.04 mm.

The helical slit 14 formed in the hollow needle 10 is a through-slit that extends from the outer peripheral surface to the inner peripheral surface of a metal pipe. A slit formed in a hollow needle in the present invention may be a blind slit that does not extend to the inner peripheral surface.

In a region of the hollow needle 10 (the distal end portion 11 and the proximal end portion 12) in which the slit 14 is formed, the pitch of the slit 14 continuously decreases in the distal end direction. Thus, the rigidity of the hollow needle 10 can be continuously (smoothly) reduced in the distal end direction, and thus the needle device has particularly good operability during introduction of the hollow needle 10 into an adrenal gland. In the present invention, the pitch of entirety of the slit formed in the hollow needle may be regular.

Figure 6:
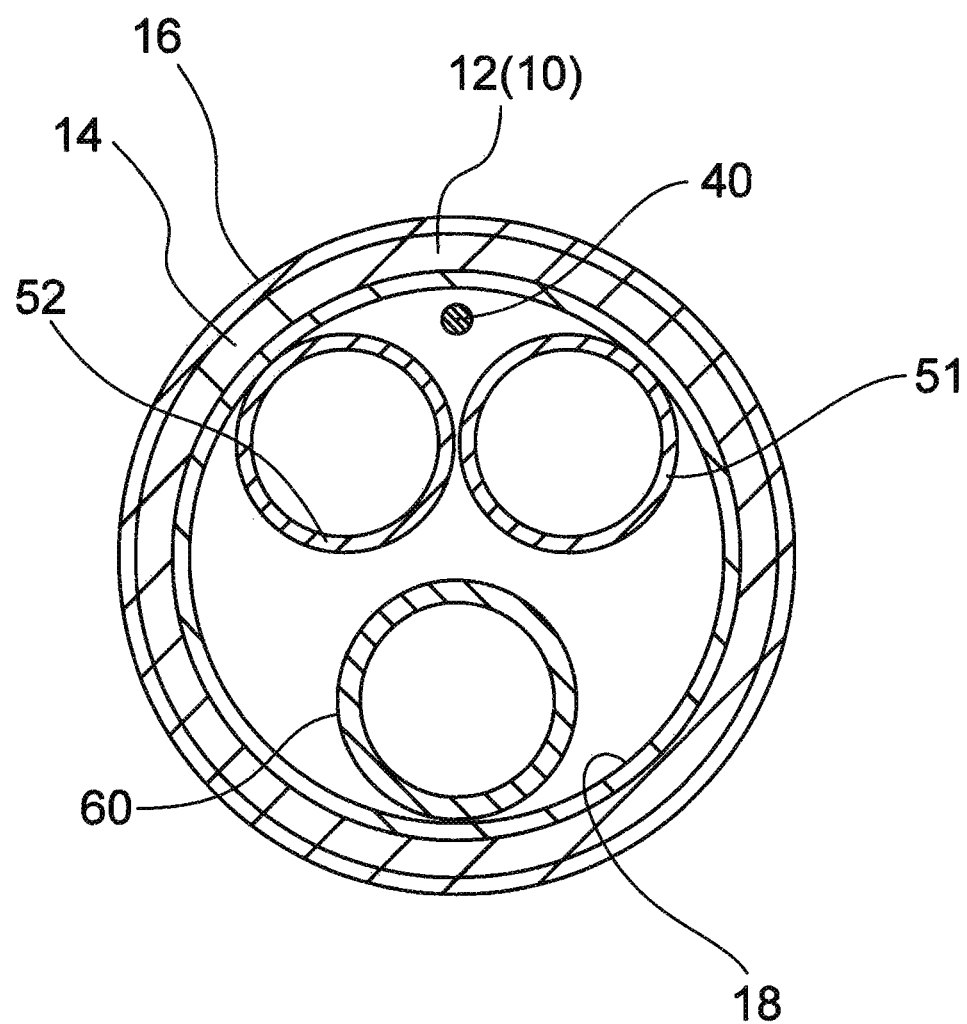
FIG. 6 is a cross-sectional view of the ablation needle device illustrated in FIG. 1 (sectional view taken along line VI-VI of FIG. 1).

As illustrated in FIG. 6, the waterproof seal coating 18 is formed on the inner peripheral surface of the hollow needle 10 over the entire length thereof, and, because waterproofing is applied in this manner, cooling liquid in the inside of the hollow needle 10 does not leak out from the slit 14 formed in the distal end portion 11.

The film thickness of the waterproof seal coating 18 is, for example, 5 to 100 μm, and preferably 20 to 60 μm.

The waterproof seal coating 18 is formed by increasing the diameter of a heat-expandable resin tube, which is in a state of having been inserted to the inside of the hollow needle 10, by heating the heat-expandable resin tube.

Examples of a heat-expandable resin tube for forming the waterproof seal coating 18 include, although not particularly limited as long as the tube has heat-expandability, include a tube made of a polyurethane resin, an FEP resin, or the like.

In the present embodiment, the waterproof seal coating 18 is formed on the inner peripheral surface of the hollow needle 10 over the entire length of the hollow needle 10. However, because the waterproofing ability (effect of preventing leaking out of cooling liquid from the slit 14) of the proximal end portion 12 of the hollow needle 10 is ensured by the coating resin 16, the waterproof seal coating 18 may be formed only on the inner peripheral surface of a region of the distal end portion 11 of the hollow needle 10 in which the slit 14 is formed.

As illustrated in FIGS. 4, 5, 7, and 8, the distal end of the hollow needle 10 (the distal end portion 11) is closed by the distal end tip 15 made of a resin, and thus cooling liquid does not leak out from the distal end of the hollow needle 10.

Examples of a resin from which the distal end tip 15 is made include a PEEK resin, nylon, polycarbonate, and the like.

As illustrated in FIGS. 1 to 3 and FIGS. 9 to 11, the hub 20 of the ablation needle device 100, which is attached to the proximal end side of the hollow needle 10, is a branched hub that includes the liquid flow port 21, the connection port 23 of an electric connector, and the guidewire port 25.

The liquid flow port 21 includes both of a "liquid injection port" for injecting cooling liquid to the inside of the hub 20 and supplying the cooling liquid to the inside of the hollow needle 10, and a "liquid discharge port" for discharging, from the hub 20, cooling liquid that has returned to the inside of the hub 20 from the inside of the hollow needle 10 after cooling the electrode.

As illustrated in FIGS. 2, 3, 9, and 11, a first extension tube 71 extends out from the flow port 21.

Figure 10:
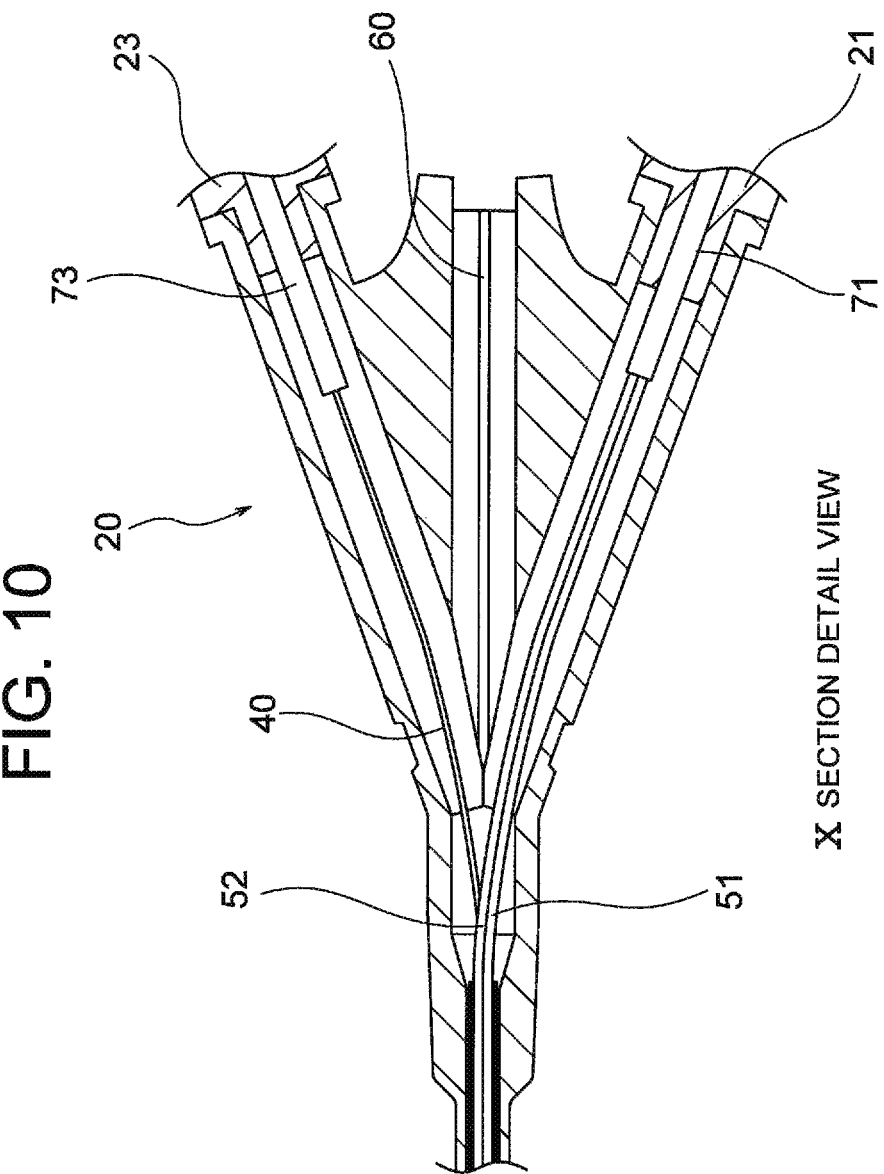
FIG. 10 is an enlarged partial longitudinal sectional view of the ablation needle device illustrated in FIG. 1 (enlarged view of portion X of FIG. 9).
Figure 11:
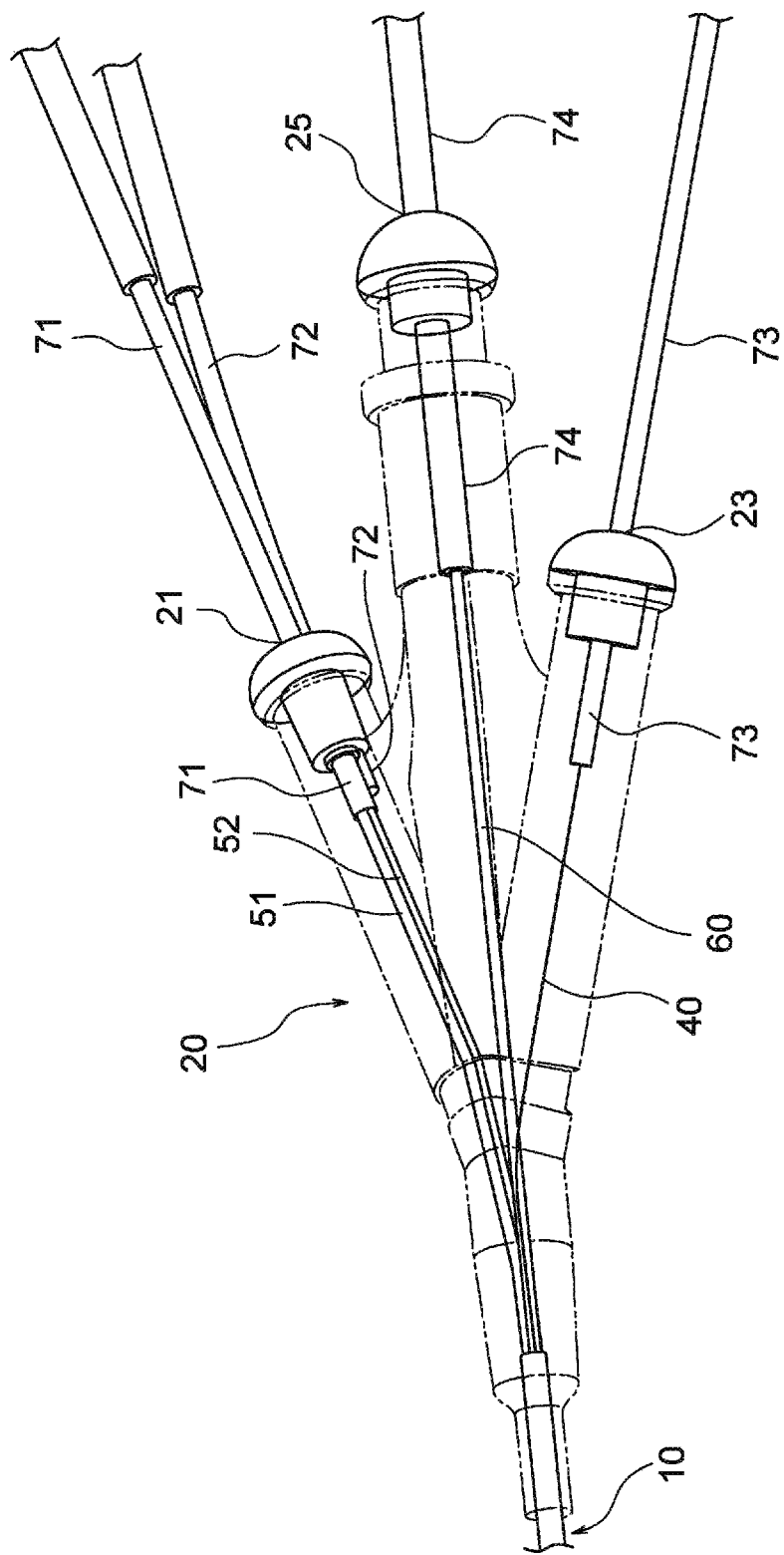
FIG. 11 is an enlarged partial perspective view of the ablation needle device illustrated in FIG. 1.

As illustrated in FIGS. 10 and 11, a proximal end portion of the first cooling liquid introducing pipe 51 and a proximal end portion of the second cooling liquid introducing pipe 52, which will be described below, are inserted into the distal end opening of the first extension tube 71 positioned in the inside of the hub 20.

A connector 76 (liquid injection connector) is attached to the proximal end of the first extension tube 71, and the first extension tube 71 is coupled, via the connector 76, to a cooling liquid supply pump of a cooling liquid circulation mechanism (and thus the flow port 21 includes a liquid injection port).

Here, examples of cooling liquid, which flows through the first extension tube 71 and is injected from the liquid flow port 21, include a high-concentration saline solution such as a saturated saline solution. The temperature of cooling liquid (saturated saline solution) injected is about −8 to −1° C.

Figure 3:
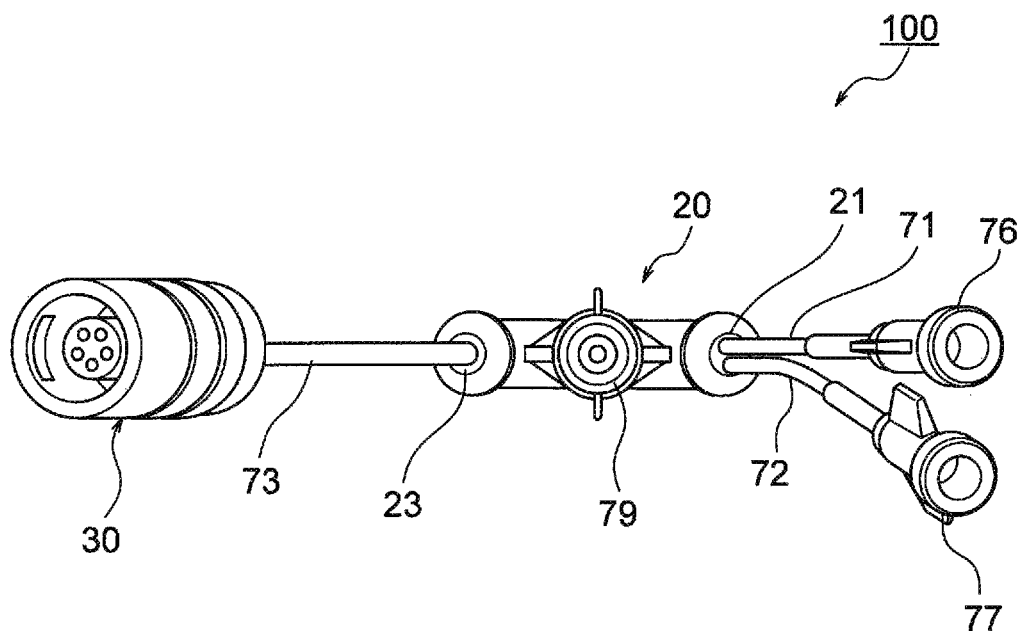
FIG. 3 is a side view of the ablation needle device illustrated in FIG. 1.

As illustrated in FIGS. 1, 3, and 11, a second extension tube 72 extends out from the flow port 21 together with the first extension tube 71.

The second extension tube 72 communicates with the inside of the hollow needle 10, because the distal end thereof is open in the inside of the hub 20.

A connector 77 (liquid discharge connector) is attached to the proximal end of the second extension tube 72, and the second extension tube 72 is coupled, via the connector 77, to a liquid recovery tank of a cooling liquid circulation mechanism (and thus the flow port 21 includes a liquid discharge port).

The connection port 23 of the electric connector is a port for inserting a lead of the electric connector 30 and the thermocouple 40 to the inside of the hub 20.

As illustrated in FIGS. 1 to 3 and FIGS. 9 and 11, a third extension tube 73 extends out from the connection port 23. The lead of the electric connector 30 and the thermocouple 40 extend through the inside of the third extension tube 73, are guided to the connection port 23, and are inserted to the inside of the hub 20.

Figure 2:
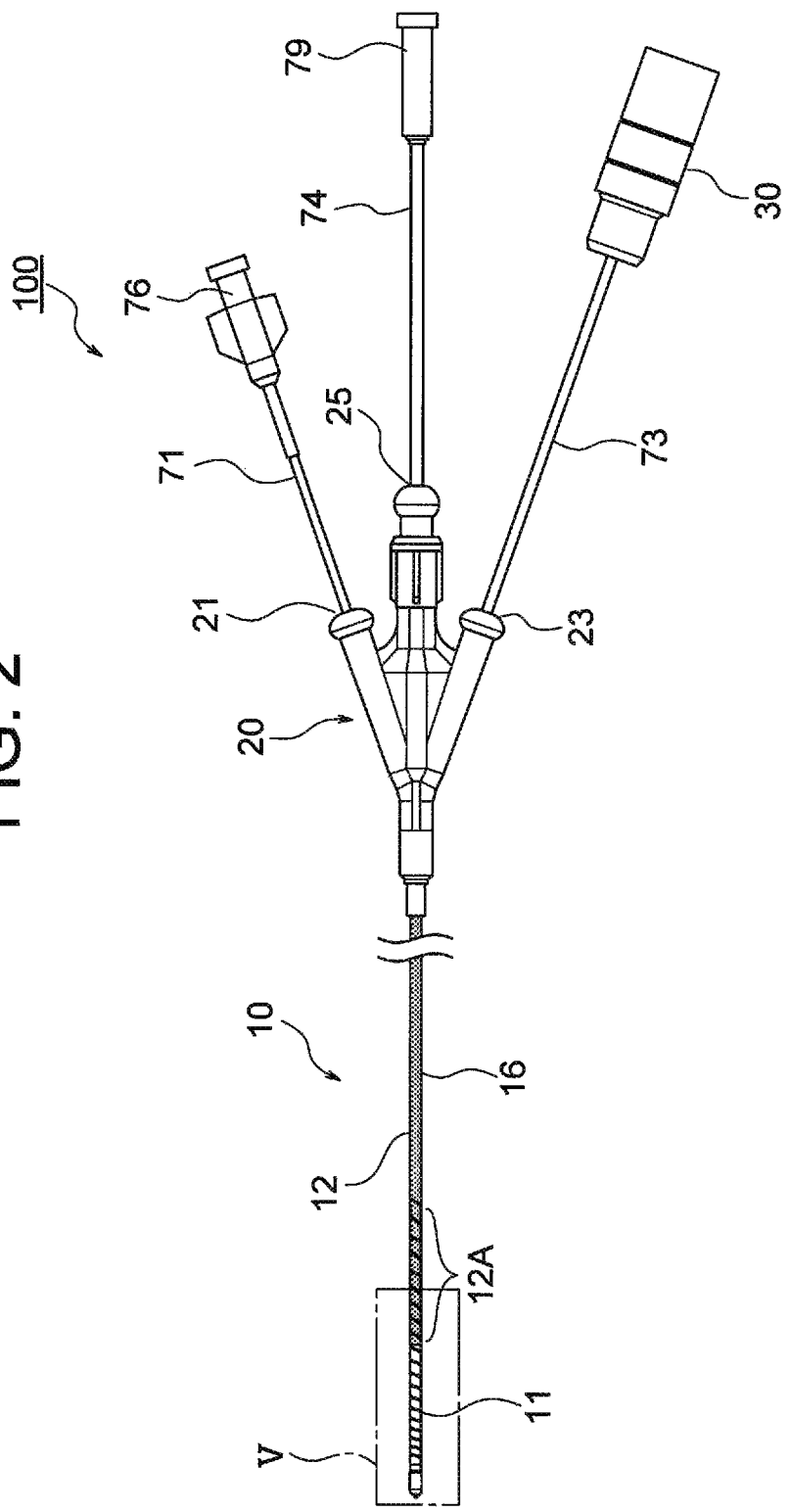
FIG. 2 is a plan view of the ablation needle device illustrated in FIG. 1.
Figure 9:
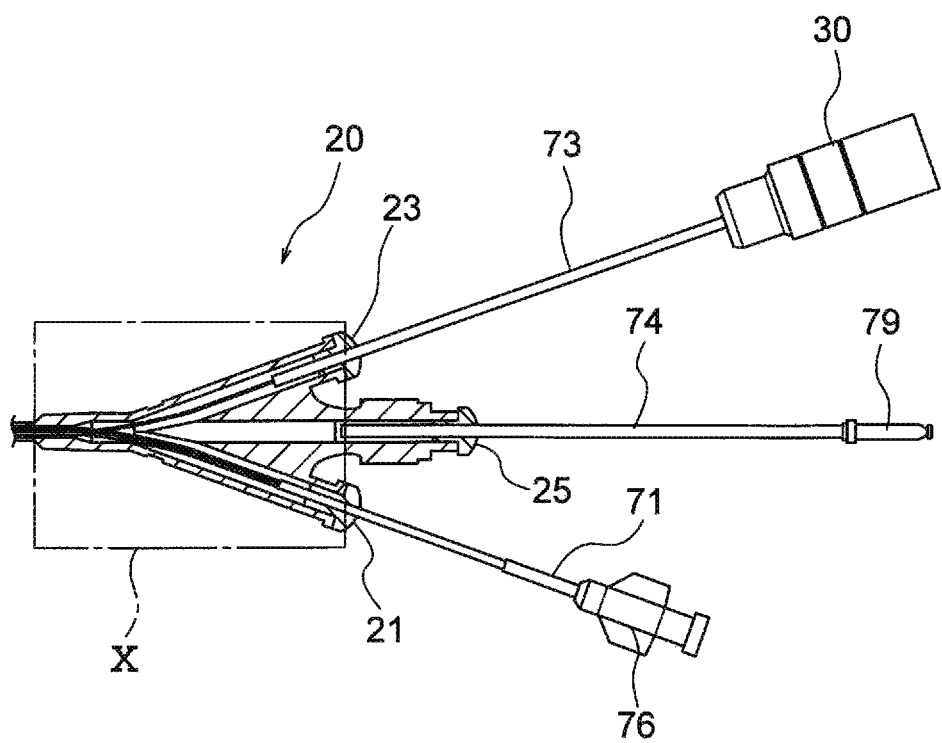
FIG. 9 is an enlarged partial longitudinal sectional view of the ablation needle device illustrated in FIG. 1 (sectional view taken along line IX-IX of FIG. 1).

As illustrated in FIGS. 2, 9, and 11, a fourth extension tube 74 extends out from the guidewire port 25.

As illustrated in FIG. 11, a proximal end portion of the lumen tube 60 forming a guidewire lumen is inserted into a distal end opening of the fourth extension tube 74 positioned in the inside of the hub 20.

A connector 79 for inserting a guidewire is attached to the proximal end of the fourth extension tube 74.

The electric connector 30 of the ablation needle device 100 is a connector for supplying a high-frequency electric current to the electrode, which is constituted by the distal end portion 11 of the hollow needle 10, by connecting this to a high-frequency electric power source device.

The lead (not shown) of the electric connector 30 extends through the inside of the third extension tube 73 and is inserted from the connection port 23 to the inside of the hub 20. The distal end of the electric connector 30 is fixed, for example, to an inner peripheral surface (metal surface that is exposed by peeling off the waterproof seal coating 18) of the proximal end portion of the hollow needle 10 by welding, and thus the electric connector 30 and the hollow needle 10 are electrically connected.

The electric connector 30 is used also as a thermocouple connector. The thermocouple 40 of the ablation needle device 100 is used to measure the temperature of a tissue around the electrode.

Figure 7:
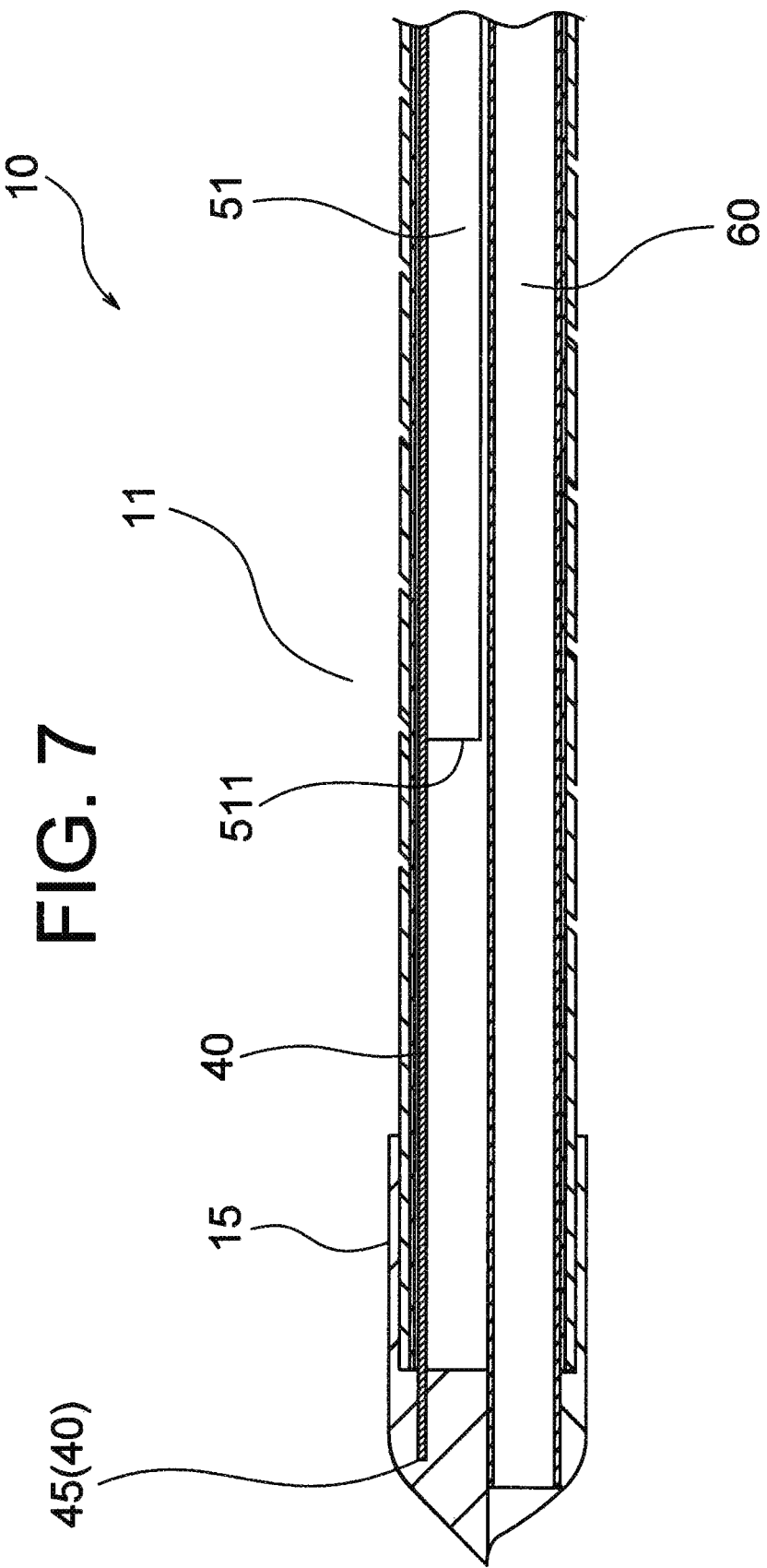
FIG. 7 is an enlarged partial longitudinal sectional view of the ablation needle device illustrated in FIG. 1 (sectional view taken along line VII-VII of FIG. 5).
Figure 8:
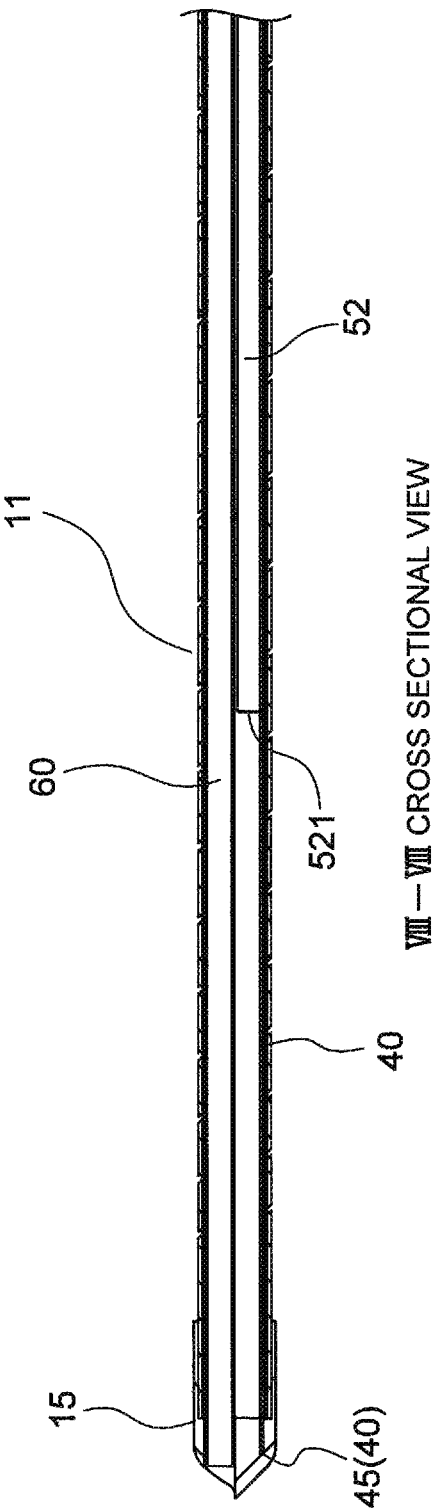
FIG. 8 is an enlarged partial longitudinal sectional view of the ablation needle device illustrated in FIG. 1 (sectional view taken along line VIII-VIII of FIG. 5).

The thermocouple 40 connected to the electric connector 30 (thermocouple connector) extends through the inside of the third extension tube 73, is inserted from the connection port 23 to the inside of the hub 20 and extends in the inside of the hub 20 as illustrated in FIGS. 10 and 11, and extends in the inside of the hollow needle 10 as illustrated in FIGS. 6 to 8.

The temperature measuring junction (temperature sensor) 45 of the thermocouple 40 is embedded in the distal end tip 15 made of a resin and closing the distal end of the hollow needle 10.

Because the temperature measuring junction 45 of the thermocouple 40 is embedded in the distal end tip 15 made of a resin having low thermal conductivity, the temperature measuring junction 45 is not easily influenced by temperature variation due to heating and cooling of the electrode (the distal end portion 11 of the hollow needle 10) having high thermal conductivity, and can accurately measure the temperature of a tissue around the electrode.

In the ablation needle device 100 according to the present embodiment, the two cooling liquid introducing pipes 51 and 52, whose distal end opening positions differ, are provided in order to ensure a flow path of cooling liquid in the inside of the hollow needle 10.

As illustrated in FIGS. 6, 7, 10, and 11, the first cooling liquid introducing pipe 51 of the ablation needle device 100 extends in the inside of the hub 20 and the inside of the hollow needle 10.

As illustrated in FIG. 7, the distal end 511 of the first cooling liquid introducing pipe 51 is positioned in the inside of the vicinity of the distal end of the distal end portion 11 of the hollow needle 10.

As illustrated in FIGS. 6, 8, 10, and 11, the second cooling liquid introducing pipe 52 of the ablation needle device 100 extends parallel to the first cooling liquid introducing pipe 51 in the inside of the hub 20 and the inside of the hollow needle 10.

As illustrated in FIG. 8, the distal end 521 of the second cooling liquid introducing pipe 52 is positioned in the inside of an approximately middle part of the distal end portion 11 of the hollow needle 10 (on the proximal end side relative to the distal end 511 of the first cooling liquid introducing pipe 51).

As illustrated in FIGS. 10 and 11, the proximal end portion of the first cooling liquid introducing pipe 51 and the proximal end portion of the second cooling liquid introducing pipe 52 are inserted into the distal end opening of the first extension tube 71 coupled to a cooling liquid supply pump.

When cooling liquid is supplied (cooling liquid is injected from the flow port 21) to a lumen of the first cooling liquid introducing pipe 51 and a lumen of the second cooling liquid introducing pipe 52 through the first extension tube 71, the cooling liquid is ejected from the distal end opening of the first cooling liquid introducing pipe 51 positioned in the vicinity of the distal end of the distal end portion 11, and is ejected from the distal end opening of the second cooling liquid introducing pipe 52 positioned in the approximately middle part of the distal end portion 11.

Cooling liquid ejected from the distal end opening of the first cooling liquid introducing pipe 51 can cool mainly a distal end part of the distal end portion 11 constituting the electrode, and cooling liquid ejected from the distal end opening of the second cooling liquid introducing pipe 52 can cool mainly a proximal end part of the distal end portion 11.

Because the distal end opening position of the first cooling liquid introducing pipe 51 and the distal end opening position of the second cooling liquid introducing pipe 52 differ from each other (the ejection positions of cooling liquid in the inside of the electrode differ) in this manner, cooling with small nonuniformity in the longitudinal direction of the electrode can be performed even when the length of the electrode constituted by the distal end portion 11 of the hollow needle 10 is large.

Moreover, because the two cooling liquid introducing pipes 51 and 52 are caused to extend in the inside of the hollow needle 10 in which the lumen tube 60 illustrated in FIG. 6 extends, the total cross-sectional area of these introducing pipes can be made larger than the cross-sectional area of one cooling liquid introducing pipe in a case where the introducing pipe is caused to extend.

Cooling liquid ejected from the distal end opening of the first cooling liquid introducing pipe 51 and the distal end opening of the second cooling liquid introducing pipe 52 cools the electrode constituted by the distal end portion 11 of the hollow needle 10 from the inside (inner cooling), then returns from the inside of the hollow needle 10 to the inside of the hub 20, and flows in the proximal-end direction in the inside of the second extension tube 72; and thus the cooling liquid is discharged from the flow port 21 and recovered to the liquid recovery tank.

As illustrated in FIGS. 6 to 8, the lumen tube 60 of the ablation needle device 100 extends in the inside of the hollow needle 10 and forms a guidewire lumen.

A distal end part of the lumen tube 60 extends through the distal end tip 15 made of a resin, and forms an opening, which serves as a guidewire port, at the distal end of the distal end tip 15. Also with this configuration, the liquid-tightness of the inside of the hollow needle 10 is ensured.

By inserting a guidewire into the guidewire lumen formed by the lumen tube 60 and introducing the ablation needle device 100, the electrode (the distal end portion 11 of the hollow needle 10) can be caused to rapidly and reliably reach a target site.

With the ablation needle device 100 according to the present embodiment, by being mounted in a high-frequency ablation treatment system described below, a high-frequency ablation treatment of an adrenal gland tumor can be performed. Moreover, because the high-frequency ablation treatment is a transvenous ablation treatment, it can be comparatively easily performed for a tumor in a left adrenal gland, which has been difficult to treat with an existing manipulation of inserting a high-frequency needle from the back.

Because the helical slit 14 is formed not only in the proximal end portion 12 of the hollow needle 10 but also in the distal end portion 11 of the hollow needle 10 constituting the electrode, the hollow needle 10 including the electrode can be made flexible even when the length of the electrode is increased, and therefore the hollow needle 10 can be caused to follow the shape of a blood vessel extending to an adrenal gland, and the electrode can be caused to reach a tumor site in the adrenal gland without injuring a vascular wall. By increasing the length of the electrode, the size of an ablation region can be increased, and thus even a manipulation of ablating the entirety of an adrenal gland can be efficiently performed.

In a state in which the liquid-tightness of the inside of the hollow needle 10 is ensured by forming the waterproof seal coating 18 on the inner surface of the hollow needle 10 and closing the distal end with the distal end tip 15, by ejecting cooling liquid from the distal end opening of the first cooling liquid introducing pipe 51 and the distal end opening of the second cooling liquid introducing pipe 52, the electrode can be sufficiently cooled while avoiding a risk that occurs when cooling liquid is irrigated by ensuring the liquid-tightness of the inside and performing inner-cooling.

Because, in the inside of the hollow needle 10, the distal end opening position of the first cooling liquid introducing pipe 51 is positioned in the vicinity of the distal end of the distal end portion 11 and the distal end opening position of the second cooling liquid introducing pipe 52 is positioned in an approximately middle part of the distal end portion 11, cooling with small nonuniformity in the longitudinal direction of the electrode can be performed even when the length of the electrode is increased.

Because the distal end tip that closes the distal end of the hollow needle 10 is made of a resin and the temperature measuring junction of the thermocouple 40 is embedded in the distal end tip 15, the temperature measuring junction is not easily influenced by temperature variation of the electrode (the distal end portion 11 of the hollow needle 10) having high thermal conductivity and can accurately measure the temperature of a tissue around the electrode.

Heretofore, an embodiment of an ablation needle device according to an embodiment of the present invention has been described. However, the present invention is not limited to these and can be modified in various ways.

For example, a hub of an ablation needle device according to the present invention may include, separately, an injection port for injecting cooling liquid and supplying the cooling liquid to the inside of the hollow needle, and a discharge port for discharging liquid that has cooled the electrode and returned from the inside of the hollow needle.

The number of cooling liquid introducing pipes (cooling liquid introducing pipes) of an ablation needle device according to the present invention is not limited to two and may be three or larger.

An ablation needle device according to the present invention can be used to treat a tumor other than an adrenal gland tumor (such as a liver cancer).

<High-Frequency Ablation Treatment System>

A high-frequency ablation treatment system 600 according to an embodiment illustrated in FIG. 12 includes: the ablation needle device 100 described above; a high-frequency electric power source device 130 connected to the electric connector 30 of the ablation needle device 100; a patient plate 150 connected to the high-frequency electric power source device 130; a guiding catheter 160 for guiding the electrode of the ablation needle device 100 to an adrenal gland AG of a patient P; and a cooling liquid circulation mechanism 120 that includes a cooling liquid supply pump 121 that injects cooling liquid into the flow port (injection port) of the hub 20 through the first extension tube 71 in order to cool the electrode of the ablation needle device 100, and a recovery tank 122 that recovers liquid that has cooled the electrode and returned from the inside of the hollow needle 10 to the inside of the hub 20 from the flow port (discharge port) through the second extension tube 72 and cools the liquid again. In the figure, 170 denotes a guidewire.

As illustrated in FIG. 12, the electric connector 30 of the ablation needle device 100 is connected to a needle device connector 131 of the high-frequency electric power source device 130. A patient plate connector 132 of the high-frequency electric power source device 130 is connected to the patient plate 150.

Thus, it is possible to cause a high-frequency electric current to flow between the distal end portion (electrode) of the hollow needle 10 of the ablation needle device 100 and the patient plate 150 (to perform a high-frequency ablation treatment of an adrenal gland tumor).

The first extension tube 71, which extends out from the flow port (injection port) of the hub 20 of the ablation needle device 100, is connected to the supply pump 121 of the cooling liquid circulation mechanism 120.

Thus, when a high-frequency ablation treatment is being performed, cooling liquid from the supply pump 121 can be injected from the flow port (injection port) to the inside of the hub 20 and supplied to the inside of the hollow needle 10, and the electrode formed from the distal end portion of the hollow needle 10 can be cooled from the inside thereof (inner cooling).

The second extension tube 72, which extends out from the flow port (discharge port) provided in the hub 20 of the ablation needle device 100, is connected to the recovery tank 122 of the cooling liquid circulation mechanism 120.

Thus, liquid that has cooled the electrode and returned from the inside of the hollow needle 10 to the inside of the hub 20 can be discharged from the flow port (discharge port) to the outside of the hub 20, and can be recovered to the recovery tank 122 through the second extension tube 72.

The liquid recovered to the recovery tank 122 is cooled (again) in the recovery tank 122, and then injected by the supply pump 121 to the inside of the hub 20.

The guiding catheter 160 of the high-frequency ablation treatment system 600 is inserted in advance so that the distal end thereof is positioned in (the vicinity of) the adrenal gland AG of the patient P in order to guide the distal end portion of the hollow needle 10 of the ablation needle device 100 to the adrenal gland.

The guiding catheter 160 schematically illustrated in FIG. 12 has different shapes respectively for a right adrenal gland and a left adrenal gland in accordance with the difference between the shapes of blood vessels extending to the adrenal glands.

Figure 13A:
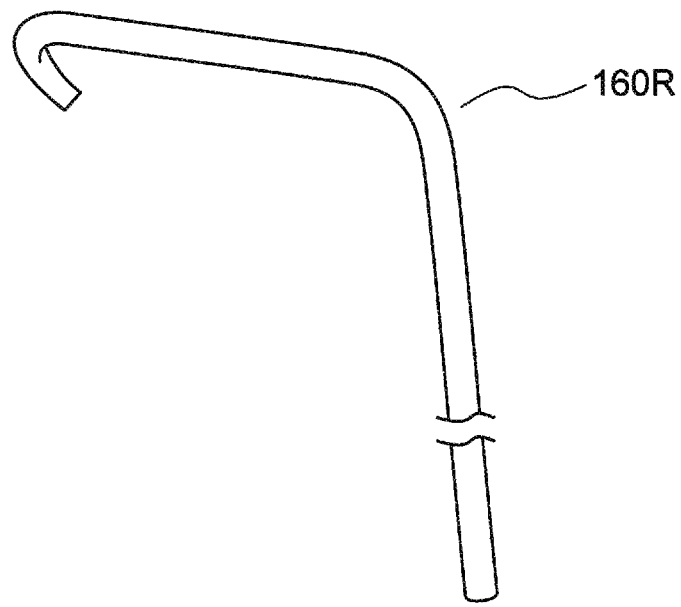
FIG. 13A illustrates the shape of a guiding catheter, for a right adrenal gland, of the high-frequency ablation treatment system according to the present invention.
Figure 13B:
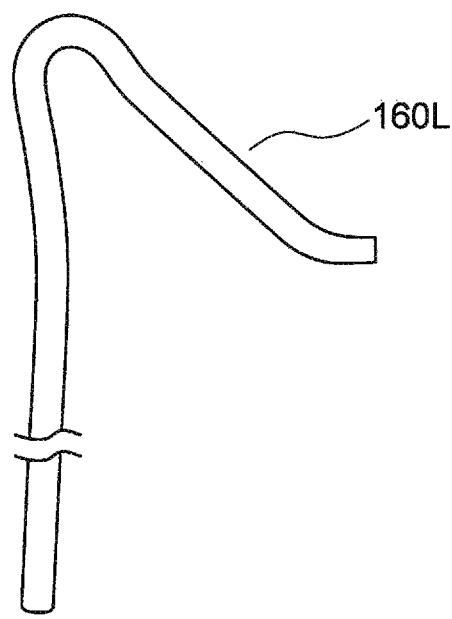
FIG. 13B illustrates the shape of a guiding catheter, for a left adrenal gland, of the high-frequency ablation treatment system according to the present invention.

FIG. 13A illustrates the shape of a distal end part of a guiding catheter 160R for a right adrenal gland. FIG. 13B illustrates the shape of a distal end part of a guiding catheter 160L for a left adrenal gland.

The guiding catheters 160R and 160L illustrated in FIGS. 13A and 13B both have a plurality of curved portions.

Figure 14A:
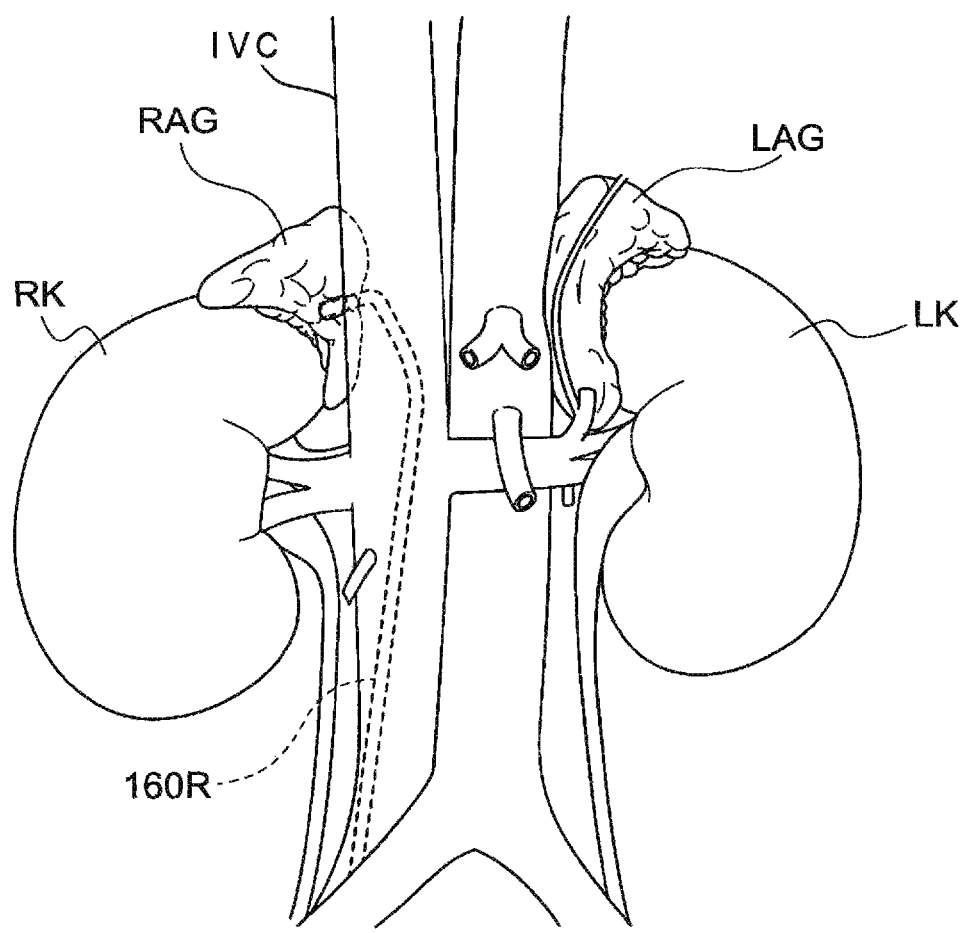
FIG. 14A illustrates a state in which the distal end of the guiding catheter illustrated in FIG. 13A has reached the right adrenal gland.
Figure 14B:
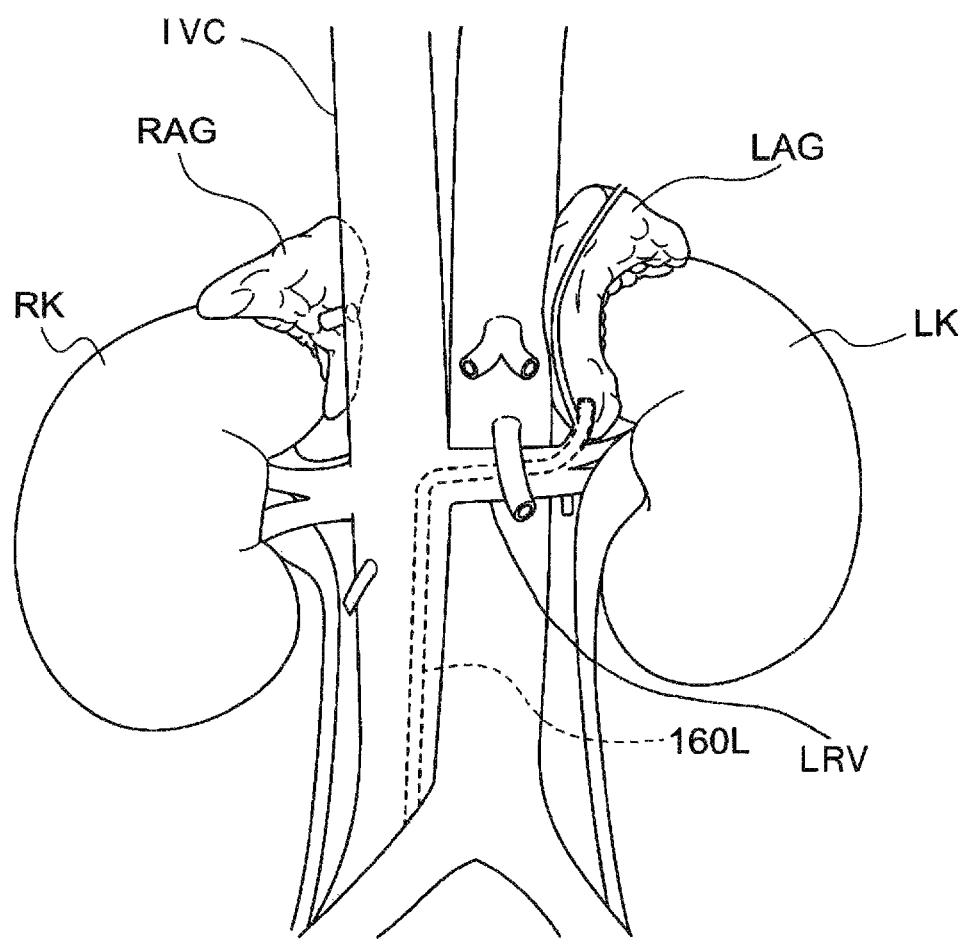
FIG. 14B illustrates a state in which the distal end of the guiding catheter illustrated in FIG. 13B has reached the left adrenal gland.

As illustrated in FIG. 14A, the guiding catheter 160R for a right adrenal gland illustrated in FIG. 13A is inserted through an inferior vena cava IVC and a right adrenal gland vein so that the distal end thereof is positioned in (the vicinity of) a right adrenal gland RAG. As illustrated in FIG. 14B, the guiding catheter 160L for a left adrenal gland illustrated in FIG. 13B is inserted through the inferior vena cava IVC, a left renal vein LRV, and a left adrenal gland vein so that the distal end thereof is positioned in (the vicinity of) a left adrenal gland LAG.

In FIGS. 14A and 14B, RK denotes a right kidney and LK denotes a left kidney.

The outside diameter of the guiding catheter 160 (160R, 160L) is, for example, 1.0 to 4.0 mm, and preferably 1.5 to 2.7 mm.

The inside diameter of the guiding catheter 160 is, for example, 0.6 to 3.1 mm, and preferably 0.75 to 2.1 mm.

The length of the guiding catheter 160 is, for example, 350 to 2100 mm, and preferably 550 to 950 mm.

As the guiding catheter 160 (160R, 160L), a catheter that has been used to sample blood from an adrenal gland vein (adrenal gland vein sampling) can be used.

With the high-frequency ablation treatment system 600 according to the present embodiment, by causing a high-frequency electric current to flow between the distal end portion of the hollow needle 10 of the ablation needle device 100 and the patient plate 150, a high-frequency ablation treatment of an adrenal gland tumor (minimally-invasive transvenous ablation treatment) can be performed.

When the high-frequency ablation treatment is being performed, by ejecting cooling liquid from the supply pump 121 of the cooling liquid circulation mechanism 120 from the distal end openings of the first cooling liquid introducing pipe and the second cooling liquid introducing pipe at the distal end portion of the hollow needle 10 of the ablation needle device 100, the electrode formed from the distal end portion of the hollow needle 10 can be cooled from the inside (inner cooling).

Heretofore, a high-frequency ablation treatment system for an adrenal gland tumor, which is an embodiment of a high-frequency ablation treatment system according to the present invention, has been described. However, a high-frequency ablation treatment system according to the present invention can be used to perform an ablation treatment of a tumor other than an adrenal gland tumor (such as a liver cancer).

REFERENCE SIGNS LIST 100 ablation needle device
10 hollow needle
11 distal end portion of hollow needle
12 proximal end portion of hollow needle
12A distal end region of proximal end portion
14 slit
15 distal end tip
16 coating resin
18 waterproof seal coating
20 hub (branched hub)
21 liquid flow port
23 connection port of electric connector
25 guidewire port
30 electric connector
40 thermocouple
45 temperature measuring junction (temperature sensor) of thermocouple
51 first cooling liquid introducing pipe
511 distal end of first cooling liquid introducing pipe
52 second cooling liquid introducing pipe
521 distal end of second cooling liquid introducing pipe
60 lumen tube
71 to 74 extension tube
76, 77, 79 connector
120 cooling liquid circulation mechanism
121 cooling liquid supply pump
122 cooled liquid recovery tank
130 high-frequency electric power source device
131 needle device connector
132 patient plate connector
150 patient plate
160 (160R, 160L) guiding catheter
170 guidewire
600 high-frequency ablation treatment system

The invention claimed is:

1. An ablation needle device for performing high-frequency ablation treatment of a tumor, comprising:
  a hollow needle that is made of a metal and that is composed of a proximal end portion having an outer surface that is insulation-coated with a resin and a distal end portion having an outer surface that is exposed and thus constituting an electrode;
  a hub that is attached to a proximal end side of the hollow needle and that includes a liquid injection Port for injecting liquid for cooling the electrode and supplying the liquid to an inside of the hollow needle, and a liquid discharge port for discharging liquid that has co led the electrode and returned from the inside of the hollow needle;
  an electric connector that is electrically connected to the hollow needle in order to supply a nigh-frequency electric current to the electrode;
  a thermocouple that extends in the inside of the hollow needle in order to measure a temperature of a tissue around the electrode; and
  a plurality of cooling introducing pipes each of which extends in an inside of the hub and the inside of the hollow needle, each of which has a distal end positioned in an inside of the distal end portion of the hollow needle, and each of which ejects liquid injected from the injection port from a distal end opening thereof,
  wherein the hollow needle is given flexibility by forming a helical slit in at least a distal end region of the proximal end portion of the hollow needle and the distal end portion,
  wherein a liquid-tightness of the inside of the hollow needle is ensured by applying waterproofing to an inner surface of the hollow needle in at least a region in which the slit is formed in the distal end portion and by closing a distal end of the hollow needle, and
  wherein distal end opening positions of the plurality of cooling liquid introducing pipes differ from each ether in a distal-proximal direction of the hollow.

2. The ablation needle device according to claim 1, wherein the hub includes a liquid flow port that includes both of the injection port and the discharge port.

3. The ablation needle device according to claim 1, comprising:
  a first cooling liquid introducing pipe that extends in the inside of the hub and the inside of the hollow needle, that has a distal end positioned in the inside of the distal end portion of the hollow needle, and that ejects liquid injected from the injection port from a distal end opening thereof; and
  a second cooling liquid introducing pipe that extends in the inside of the hub and the inside of the hollow needle together with the first cooling liquid introducing pipe, that has a distal end positioned in the inside of the distal end portion of the hollow needle, and that ejects liquid injected from the injection port from a distal end opening thereof,
  wherein the distal end opening position of the first cooling liquid introducing pipe and the distal end opening position of the second cooling liquid introducing pipe differ from each other in the distal-proximal direction of the hollow needle, and wherein the plurality of cooling liquid introducing pipes include the first cooling liquid introducing pipe and the second cooling liquid introducing pipe.

4. The ablation needle device according to claim 3, wherein the distal end opening of the first cooling liquid introducing pipe is positioned in an inside of a vicinity of distal end of the distal end portion of the hollow needle, and the distal end opening of the second cooling liquid introducing pipe is positioned in an inside of an approximately middle part or a vicinity of a proximal end of the distal end portion of the hollow needle.

5. The ablation needle device according to claim 1, wherein the distal end of the hollow needle is closed by a distal end tip that is made of a resin, and
wherein a temperature measuring junction of the thermocouple is embedded in the distal end tip.

6. The ablation needle device according to claim 1, wherein a lumen tube that forms a guidewire lumen extends in the inside of the hollow needle.

7. The ablation needle device according to claim 1, wherein a length of the electrode constituted by the distal end portion of the hollow needle is 6 to 30 mm.

8. The ablation needle device according to claim 1, wherein a pitch of the slit formed in the hollow needle continuously or intermittently decreases in a distal end direction.

9. The ablation needle device according to claim 1, wherein, in at least the region in which the slit is formed in the distal end portion, a waterproof seal coating is formed on the inner surface of the hollow needle.

10. The ablation needle device according to claim 9, wherein the waterproof seal coating is formed by a heat-expandable resin tube that increases its diameter by being heated, which is in a state of having been inserted to the inside of the hollow needle.

11. The ablation needle device according to claim 1, wherein the hollow needle is configured to be transvenously introduced into an adrenal gland for performing an ablation treatment of an adrenal gland tumor.

12. A high-frequency ablation treatment system for a tumor, comprising:
the ablation needle device according to claim 1;
a high-frequency electric power source device connected to the electric connector;
a patient plate connected to the high-frequency electric power source device;
a guiding catheter for guiding the distal end portion of the hollow needle to a vicinity of a target site; and
a cooling liquid circulation mechanism that includes a cooling liquid supply pump that injects cooling liquid into the injection port of the hub in order to cool the electrode of the ablation needle device, and a recovery tank that recovers liquid that has cooled the electrode and returned from the inside of the hollow needle to the inside of the hub from the discharge port and cools the liquid again.

* * * * *